United States Patent [19]

Drent

[11] Patent Number: 5,227,561
[45] Date of Patent: Jul. 13, 1993

[54] CO-DIMERIZATION OF VINYL AROMATICS WITH α-MONOOLEFINS

[75] Inventor: Eit Drent, Amsterdam, Netherlands

[73] Assignee: Shell Oil Company, Houston, Tex.

[21] Appl. No.: 928,399

[22] Filed: Aug. 12, 1992

[30] Foreign Application Priority Data

Aug. 23, 1991 [EP] European Pat. Off. ........ 91202164.9

[51] Int. Cl.$^5$ ................................................ C07C 2/24
[52] U.S. Cl. .................................. 585/514; 585/510; 585/511; 585/520; 585/527; 585/452
[58] Field of Search ............... 585/509, 510, 511, 452, 585/514, 520, 527

[56] References Cited

U.S. PATENT DOCUMENTS 3,920,763 11/1975 Yoo et al. ............................ 585/511
4,786,623 11/1988 Grenouillet et al. ............... 502/154

*Primary Examiner*—Asok Pal
*Assistant Examiner*—P. Achutamurthy

[57] ABSTRACT

The invention concerns a process for the co-dimerization of a vinyl aromatic monomer (e.g. styrene) with an α-monoolefin monomer (e.g. ethylene, propylene or 1-butylene), using a catalyst composition comprising palladium, an anion of a strong acid and an aliphatic diphosphine.

8 Claims, No Drawings

CO-DIMERIZATION OF VINYL AROMATICS WITH α-MONOOLEFINS

FIELD OF THE INVENTION

This invention relates to a homogeneous catalytic process for the co-dimerization of a vinyl aromatic compound with an alpha-monoolefin (α-monoolefin) monomer or a derivative thereof.

BACKGROUND OF THE INVENTION

A number of catalyst systems are known for the reactions between a vinyl aromatic compound and an α-monoolefin. Examples are the use of rhodium chloride in the reaction of styrene with ethylene (U.S. Pat. No. 3,013,066) and the use of palladium chloride in the same reaction (J. Orgmet. Chem. 21, 1970. 218). However, the yields of the products obtained by these processes have not been sufficiently high per industrial purposes.

U.S. Pat. No. 3,803,254 discloses a process of cooligomerization of a vinyl aromatic monomer with an α-monoolefin, in the presence of a cationic palladium complex prepared by treating a palladium compound with a reagent containing a complex fluoro anion or a perchlorate anion and with a trivalent organo phosphorus ligand. This palladium complex is inherently unstable, and in order to counter catalyst decomposition by precipitation of metallic palladium the patent recommends the addition of a Lewis acid.

The preparation and maintenance of these catalyst systems are relatively cumbersome and expensive.

In EP-A-0376364, a process is disclosed for the preparation of polymers of carbon monoxide with one or more α-olefins having at least three carbon atoms in the molecule, whereby a catalyst composition is used which is based upon:
a) a palladium compound,
b) an anion of an acid with a pKa of less than 2, and
c) a diphosphine of the general formula $R^1R^2P$-X-$PR^3R^4$, in which, $R^1$, $R^2$, $R^3$ and $R^4$ represent the same or different optionally polar-substituted aliphatic hydrocarbyl groups and X is a bivalent organic bridging group containing at least two carbon atoms in the bridge.

It has now been found that this catalyst composition can be used to great advantage in the process for the co-dimerization of a vinyl aromatic monomer with an o-monoolefin monomer or a derivative thereof, giving good conversion and excellent selectivity, and that the catalyst composition is very simple to prepare and very stable in this co-dimerization reaction.

SUMMARY OF THE INVENTION

The invention therefore relates to a homogeneous catalytic process for the co-dimerization of a vinyl aromatic monomer with an α-monoolefin monomer or a derivative thereof, wherein the monomers are contacted with a solution of a catalyst composition comprising:
a) a palladium compound,
b) an anion of an acid with a pKa of less than 2, and
c) a diphosphine of the general formula in which $R^1R^2P$-X-$PR^3R^4$, in which $R^1$, $R^2$, $R^3$ and $R^4$ represent the same or different unsubstituted or polar-substituted aliphatic hydrocarbyl groups and X is a bivalent organic bridging group containing at least two carbon atoms in the bridge.

DESCRIPTION OF THE PREFERRED EMBODIMENTS

The vinyl aromatic monomers according to the invention may be styrene or derivatives thereof, such as the alkyl, aryl, alkenyl, carbohydroxyl, phenyl, nitrile, halogen, ether, ester, amino or amido derivative of styrene. Unsubstituted styrene is preferred.

The α-monoolefin monomers according to the invention are linear or branched, having preferably 2 to about 8 carbon atoms. Optionally, they are polar-substituted, by e.g. aryl, alkenyl, carboxyhydroxyl, phenyl, nitryl, halogen, ether, ester amino or amido groups. Preferred α-monoolefins are ethylene, propylene and 1-butylene.

Suitably from about 0.01 to about 100, preferably from about 0.1 to about 10, moles of the vinyl aromatic compound can be reacted per mole of α-monoolefin or derivative thereof. Most preferably, however, an excess of the vinyl aromatic compound in relation to the α-monoolefin is used.

An appropriate reaction temperature is from about 20.C to about 150° C., preferably from about 40° C. to about 120° C., more preferably from about 60° C. to about 100° C.

The reaction pressure can vary from atmospheric to about 10,000 kPa, according to the reactants used and the desired product selectivity. Higher pressures, although possible, are generally economically unattractive.

The reaction time likewise can vary within wide ranges, suitably between about 0.1 and about 100 hours. When one of the reactants is consumed, the reaction should generally be terminated.

Suitable solvents for the catalytic composition are the lower aliphatic alcohols, preferably methanol, and mixtures thereof with cyclic ethers such as tetrahydrofuran. Alternatively, one of the liquid reactants, such as styrene, can also be used as a solvent for the catalytic composition.

The palladium compound employed in the catalyst composition as component a) is preferably a palladium salt. Examples of salts include salts of nitric acid; sulfuric acid; sulfonic acids, for example chlorosulfonic acid, methanesulfonic acid, trifluoromethane sulfonic acid, t-butylsulfonic acid, p-toluenesulfonic acid, or a sulfonated ion exchange resin; and a carboxylic acid, for example an alkanoic acid such as acetic acid or trifluoro acetic acid. Since halide ions can be corrosive, the palladium compound is preferably not a halide.

A preferred palladium salt is palladium acetate.

The quantity of palladium compound employed is suitably from about $10^{-7}$ to about $10^{-2}$, preferably about $10^{-5}$ to about $10^{-3}$ mol per mol of substrate.

Examples of suitable acids with a pKa of less than 2 (when determined in aqueous solution at 18° C.) are mineral acids, such as perchloric acid, sulfonic acids, such as para-toluenesulfonic acid, and halogen carboxylic acids, such as trifluoroacetic acid. In the catalyst compositions, component b) is preferably taken up in the form of an acid and/or in the form of a salt. Very suitable acids are trifluoromethane sulfonic acid and paratoluene sulfonic acid. A very suitable salt is nickel perchlorate. Preferably, the quantity of component b) present in the catalyst compositions is from about 0.5 to about 50 and in particular from about 1 to about 25 mol per mol of palladium.

In the diphosphines of the general formula $R^1R^2P$-X-$PR^3R^4$ that are eligible to be used as component c) in the catalyst compositions, groups $R^1$, $R^2$, $R^3$ and $R^4$ each preferably contain from 1 to about 10, more preferably from about 2 to about 4 carbon atoms. Optionally, groups $R^1$ and $R^2$ on the one hand, and $R^3$ and $R^4$ on the other hand may be connected to one another through a carbon-carbon bond, so that together with the phosphorus atom to which they are bound, they form a heterocyclic phosphorus-containing group. Preferably, groups $R^2$, $R^3$ and $R^4$ are the same alkyl groups. As regards the bridging group X present in the diphosphines, preference is given to bridging groups containing from 2 to about 10 atoms in the bridge, more preferably from about 3 to about 5 atoms, at least two of which are carbon atoms. Examples of suitable bridging groups R are the —CH$_2$—CH$_2$—CH$_2$— group, the —CH$_2$C(CH$_3$)$_2$—CH$_2$— group and the —CH$_2$—Si(CH$_3$)$_2$—CH$_2$— group.

Examples of diphosphines which can be used as component c) in the present catalyst composition are:

1,3-bis(di-n-butylphosphino) propane,
1,3-bis(diethylphosphino) propane,
1,3-bis(di-iso-propylphosphino) propane,
1,3-bis(dibenzylphosphino) propane,
1,2-bis(di-n-butylphosphino) ethane, and
1,4-bis(di-iso-propylphosphino) butane.

Preferably, the diphosphines are used in the catalyst composition in a quantity of from about 0.5 to about 2 and in particular of from about 0.75 to about 1.5 mol per mol of palladium.

It has surprisingly been found that compositions, differing from the compositions as described hereinbefore only in that any of the four groups $R^1$, $R^2$, $R^3$ or $R^4$ is an aromatic hydrocarbyl group cannot catalyze the co-dimerization reaction of the invention.

The products of the process according to the invention are mainly codimers of the reactant monomers, whereby different isomers can occur. For example, when the reactant monomers are ethylene and styrene the product dimers may be mainly one, or more, of the following isomers of butenylbenzene:

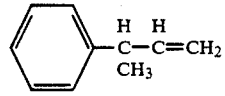

3-phenyl-butene-1

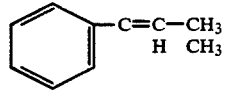

1-phenyl-isobutene-1

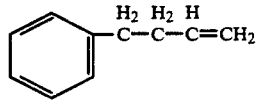

4-phenyl-butene-1

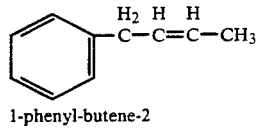

1-phenyl-butene-2

However, dimers of each of the reactants, such as styrene dimer in the above exemplary reaction, may also be formed.

An important element of the present invention is that, by varying reaction conditions, such as the temperature, pressure and duration of the reaction, a desired product (isomer) can be produced preferentially. In the above exemplary co-dimerization of ethylene and styrene a reaction temperature of below about 90° C. has been found to result in preferentially producing the branched isomers of butenylbenzene while a reaction temperature of about 90° C. to about 120° C. resulted in preferentially producing the linear isomers. Likewise, in the same exemplary reaction a relatively low pressure tends to result in the preferential production of the branched isomers while a relatively high pressure tends to produce more of the straight isomers.

After the reaction is terminated, the products may be separated according to any suitable method as are known in the art, such as distillation or extraction methods.

The codimers which are the products of the process according to the invention are useful as intermediates in organic synthesis, such as the synthesis of various aldehydes, carboxylic acids, esters, alcohols and amines.

The invention will now be further described by the following Examples which are illustrative and are not intended to be construed as limiting the scope of the invention.

EXAMPLES 1-6

A 250 ml magnetically-stirred autoclave was charged with 40 ml methanol, 20 ml (or 50 ml) styrene and 10 ml of a solution in methanol of the catalyst composition which was previously prepared and kept under nitrogen atmosphere. Subsequently the autoclave was pressurized with ethylene upto a pressure of 2000 kPa. The autoclave was sealed, heated to a temperature of 70° C. (or 80° C.) and maintained at that temperature for 5 hours. After terminating the reaction, a sample of the contents of the autoclave was analyzed by gas liquid chromatography. From the results, the mol percentage of styrene conversion was determined as well as the mol percentage of the branched butenyl benzene isomer 3-phenyl-butene-1 and the mol percentage of styrene dimer in the reaction product, both calculated in relation to converted styrene. The latter two values are illustrative of the selectivity of the reaction.

Further particulars of the reaction conditions (amount of styrene reactant, catalyst compositions, reaction temperature) and of the results are presented in the Table.

TABLE

| | Reaction conditions | | | | Results, mol % | | |
|---|---|---|---|---|---|---|---|
| Ex. | styrene monomer (ml) | T °C. | catalyst composition, compounds | mol | styrene conversion | to 3-phenyl-butene-1 | to styrene dimer |
| 1 | 20 | 80 | Pd(CH$_3$COO)$_2$ | 0.25 | 60 | 85 | 4 |
| | | | (C$_4$H$_9$)$_2$P(CH$_2$)$_3$P(C$_4$H$_9$)$_2$ | 0.30 | | | |
| | | | CF$_3$SO$_3$H | 0.50 | | | |

| | Reaction conditions | | | | Results, mol % | | |
|---|---|---|---|---|---|---|---|
| Ex. | styrene monomer (ml) | T °C. | catalyst composition, compounds | mol | styrene conversion | to 3-phenyl-butene-1 | to styrene dimer |
| 2 | 20 | 80 | $Pd(CH_3COO)_2$ | 0.25 | 70 | 86 | 2 |
| | | | $(C_2H_5)_2P(CH_2)_3P(C_2H_5)_2$ | 0.30 | | | |
| | | | $CF_3SO_3H$ | 0.50 | | | |
| 3 | 50 | 70 | $Pd(CH_3COO)_2$ | 0.25 | 55 | 84 | 10 |
| | | | $(C_2H_5)_2P(CH_2)_3P(C_2H_5)_2$ | 0.30 | | | |
| | | | $CF_3SO_3H$ | 0.50 | | | |
| 4 | 20 | 70 | $Pd(CH_3COO)_2$ | 0.25 | 50 | 90 | 5 |
| | | | $(C_2H_5)_2P(CH_2)_3P(C_2H_5)_2$ | 0.30 | | | |
| | | | $CH_3\text{-C}_6H_4\text{-}SO_3H$ | 0.50 | | | |
| 5 | 20 | 70 | $Pd(CH_3COO)_2$ | 0.25 | 85 | 65 | 7 |
| | | | $P(C_4H_9)_3$ | 0.60 | | | |
| | | | $CF_3SO_3H$ | 0.50 | | | |
| 6 | 20 | 70 | $Pd(CH_3COO)_2$ | 0.25 | —* | — | — |
| | | | $(C_6H_5)_2P(CH_2)_3P(C_6H_5)_2$ | 0.30 | | | |
| | | | $CF_3SO_3H$ | 0.50 | | | |

*no conversion

Examples 1–4 are according to the invention. They show good styrene conversion and excellent selectivity.

Examples 5 and 6 are not according to the invention. In Example 5, a monophosphine was used in the catalytic composition, resulting in a much lower selectivity. In addition, a precipitate of metallic Pd was formed during the reaction, indicating catalyst decomposition. In Example 6, a diphosphine having four aromatic hydrocarbyl groups was used in the composition, which proved not to be able to catalyze the dimerization reaction. Even after the reaction time was extended to 18 hours, only traces of codimers were found (less than 1% conversion).

EXAMPLE 7

Example 2 was repeated, except that the α-monoolefin used was 20 ml of propylene (resulting in an initial pressure of 600 kPa) and the reaction temperature was 70° C.

The styrene conversion was 60 mol %, and of the converted styrene, the amount of the (branched) isomer 2-methyl-3-phenyl-butene-1

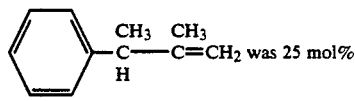

was 25 mol % and the amount of the styrene dimer was 70 mol %.

EXAMPLE 8

Example 1 was exactly repeated, except that the reaction temperature was 120° C.

The styrene conversion was now close to 100 mol %. Of the converted styrene, 62 mol % was the straight butenylbenzene isomer 1-phenyl-butene-1 and 1 mol % was styrene dimer.

EXAMPLE 9

Example 8 was repeated, except that the diphosphine used was 1,3-bis(di-iso-propylphosphino)propane, $(iC_3H_7)_2P(CH_2)_3P(ic_3H_7)_2$.

The styrene conversion was again close to 100 mol % and of the converted styrene, 75 mol % was the straight butenylbenzene isomer 1-phenyl-butene-1 and less than 1 mol % was styrene dimer.

What is claimed is:

1. A homogeneous catalytic process for the co-dimerization of styrene with an α-monoolefin monomer selected from the group consisting of ethylene, propylene and 1-butylene or a derivative thereof, which comprises contacting styrene and the α-monoolefin monomer with a solution of a catalyst comprising:
   a) a palladium compound
   b) an anion of an acid with a pKa of less than 2, and,
   c) a diphosphine of the general formula $R^1R^2P\text{-}X\text{-}PR^3R^4$, in which $R^1R^2$, and $R^3$ and $R^4$ represent the same or a different unsubstituted or polar-substituted aliphatic hydrocarbyl groups and X is bivalent organic bridging group containing at least tow carbon atoms in the bridge.

2. The process according to claim 1 wherein the palladium compound used is a palladium salt.

3. The process according to claim 2, wherein the palladium salt is palladium acetate.

4. The process according to claim 1, wherein the acid used is selected from the group consisting of trifluoromethane sulfonic acid and paratoluene sulfonic acid.

5. The process according to claim 1, wherein $R^1$, $R^2$, $R^3$ and $R^4$ each contain from 1 to about 10 carbon atoms.

6. The process according to claim 5, wherein $R^1$, $R^2$, $R^3$ and $R^4$ are the same unsubstituted alkyl groups, said alkyl groups having from 2 to about 4 carbon atoms.

7. The process according to claim 1, wherein the bridging group X contains from 2 to about 10 atoms in the bridge, at least two of which are carbon atoms.

8. The process according to claim 1, wherein the diphosphine used is selected from the group consisting of
   1,3-bis(di-n-butylphosphino) propane,
   1,3-bis(diethylphosphino) propane,
   1,3-bis(di-iso-propylphosphino) propane,
   1,3-bis(dibenzylphosphino) propane,
   1,2-bis(di-n-butylphosphino) ethane, and
   1,4-bis(di-iso-propylphosphino) butane.

* * * * *